United States Patent
Ernryd

(10) Patent No.: US 6,660,160 B1
(45) Date of Patent: Dec. 9, 2003

(54) APPARATUS FOR SEPARATION OF SOLIDS FROM A LIQUID

(75) Inventor: Leif Ernryd, Eskilstuna (SE)

(73) Assignee: Sweden Recycling AB, Hovmantorp (SE)

( * ) Notice: Subject to any disclaimer, the term of this patent is extended or adjusted under 35 U.S.C. 154(b) by 0 days.

(21) Appl. No.: 09/418,755

(22) Filed: Oct. 15, 1999

Related U.S. Application Data

(63) Continuation of application No. PCT/SE98/00685, filed on Apr. 14, 1998.

(30) Foreign Application Priority Data

Apr. 15, 1997 (SE) ................................................. 9701390

(51) Int. Cl.⁷ .......................... B01D 21/00; B01D 27/14; B01D 29/52
(52) U.S. Cl. ....................... 210/283; 210/284; 210/288; 210/316; 210/320; 210/323.1; 210/336; 210/340; 210/521; 210/522; 210/532.1
(58) Field of Search ................................. 210/224, 226, 210/231, 256, 314–317, 513, 521–522, 265, 268, 767–768, 800, 802–804, 532.1, 320, 323.1, 340, 287–288, 284, 283, DIG. 5, 537, 539, 335, 337, 338, 336

(56) References Cited

U.S. PATENT DOCUMENTS

| | | | | |
|---|---|---|---|---|
| 1,804,743 A | * | 5/1931 | Cannon | |
| 3,339,740 A | * | 9/1967 | Starzyk | |
| 3,812,970 A | * | 5/1974 | Yamazaki | 210/316 |
| 3,852,199 A | * | 12/1974 | Wachsmuth et al. | 210/522 |
| 3,925,205 A | * | 12/1975 | Sparham | 210/73 |
| 3,957,656 A | * | 5/1976 | Castelli | 210/521 |
| 4,278,545 A | * | 7/1981 | Batutis et al. | 210/521 |
| 4,333,835 A | * | 6/1982 | Lynch | 210/305 |
| 4,419,107 A | | 12/1983 | Roydhouse | |
| 4,591,437 A | * | 5/1986 | Ernryd et al. | 210/265 |
| 4,895,652 A | * | 1/1990 | Cornelissen | 210/320 |
| 4,897,206 A | * | 1/1990 | Castelli | 210/791 |
| 5,114,578 A | * | 5/1992 | Sundstrom | 210/256 |
| 5,326,474 A | * | 7/1994 | Adams et al. | 210/519 |
| 5,429,752 A | * | 7/1995 | Presby | 210/802 |
| 5,554,301 A | * | 9/1996 | Rippetoe et al. | 210/748 |
| 5,762,810 A | * | 6/1998 | Pelton et al. | 210/799 |
| 6,056,128 A | * | 5/2000 | Glasgow | 210/521 |

FOREIGN PATENT DOCUMENTS

| | | | |
|---|---|---|---|
| DE | 4243239 | * | 6/1994 |
| EP | 0 445 093 | | 9/1991 |
| EP | 691151 | * | 1/1996 |
| GB | 2039766 | * | 8/1980 |
| JP | 401034489 A | * | 2/1989 |
| JP | 401139188 A | * | 5/1989 |
| SE | 469510 | * | 7/1993 |

* cited by examiner

Primary Examiner—W. L. Walker
Assistant Examiner—Marianne Ocampo
(74) Attorney, Agent, or Firm—Young & Thompson

(57) ABSTRACT

A separation apparatus, in particular intended for separation of amalgam from water, includes a pre-settling chamber, a distribution chamber and a fine settling zone. The fine settling zone includes a plate package, with a plurality of plates fixed with spacing, forming settling channels. The plates can be machined so that they are provided with a large number of fine bumps and recesses.

17 Claims, 1 Drawing Sheet

APPARATUS FOR SEPARATION OF SOLIDS FROM A LIQUID

Figure 1:
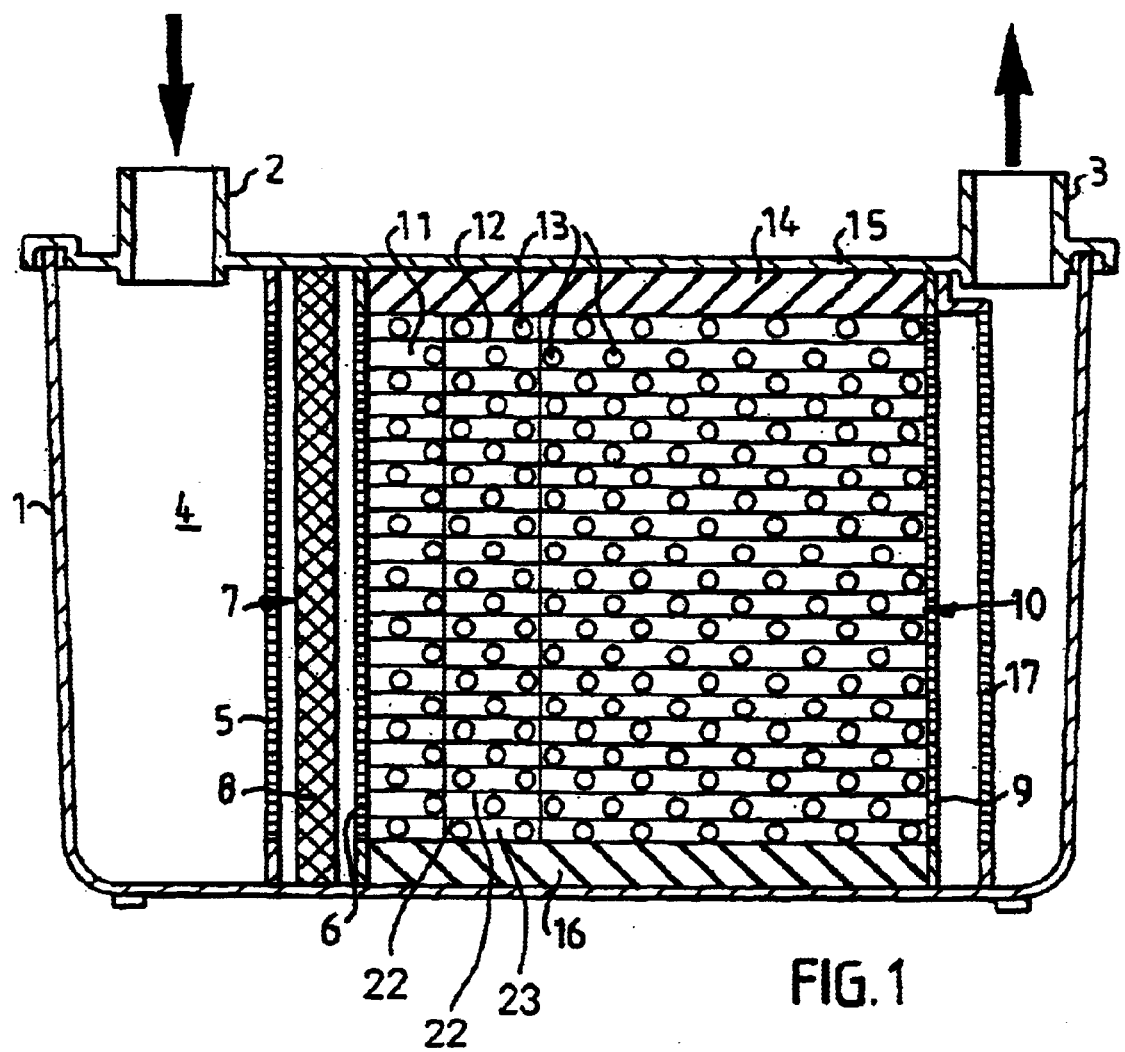

This is a continuation of co-pending international application No. PCT/SE98/00685 filed on Apr. 14, 1998 which designated the United States of America.

FIELD OF THE INVENTION

This invention relates to an apparatus for separation of solids from a liquid and in particular an apparatus for separation of amalgam from water.

BACKGROUND OF THE INVENTION

Discharge of amalgam as a source of mercurial poisoning has resulted in increasingly demands for amalgam separation from dentisteries. The proposed apparatus for dentisteries for amalgam separation are based on the standard operations, such as centrifugation, filtration, settling and combinations thereof.

Centrifugation apparatus suffer from disadvantages, such as complexity, cost and operational disturbance inter alia due to rotor imbalance caused by fouling.

Filtration apparatus, for instance that disclosed in EP-A1-0 691 151, faces problems with through flow capacity due to high pressure loss. To be able to filtrate amalgam particles of $\mu$-size, very fine filters are required. To achieve suitable through flow high external pressure is required by means of external pumping equipment risking break down.

DE-A-4 243 239 discloses an apparatus comprising two serial connected settling containers and also filtration stages in front of the inlet in each of the containers. Furthermore, the apparatus also comprises a membrane pump and a cyclone separator, whereby disadvantages with complex apparatus, such as cost of apparatus, size and regeneration problems are obvious.

For the separation of solids from liquids by pure settling, there are known a large number of apparatuses, based on the principle of laminar flow trough channels between corrugated or planar lamellas. Especially for separation of amalgam, SE-B-469 510 discloses a settling apparatus, consisting of a large number of contacting tubes, offering a substantial sedimentation surface. However, such tube packages are hard to recondition for reuse. Furthermore, smooth plastic surfaces in open tubes does not offer optimum adhesion of settled amalgam sludge bearing in mind that extreme apparatus vibrations and unexpected fluctuations in flow very well may occur during long continuous time of operation, even months, which is required because of practical reasons in a dentistry.

SUMMARY OF THE INVENTION

The object of the present invention is to provide a simple amalgam separator having a high degree of separation and safe retention capability with respect to amalgam during a relatively long time of operation, and which is also easy to clean from amalgam for reuse.

This object is attained according to the invention by an apparatus, which in the direction of flow for the liquid, which is to be cleaned from amalgam, comprises a pre-settling zone, a distribution zone and finally a fine settling zone, which consists of a plate package having a plurality of fixed plates spaced apart substantially parallel to each other, and which preferably, at least on the upper side have a large number of fine bumps and recesses provided by procedures known in the art.

By means of the plate package, being the critical part of the separator according to the invention, a large total settling area and short settling distances are obtained. Using for instance 30–60 plates, each having a surface of 2 dm$^2$, the flat settling area will be 60–120 dm$^2$. The specific settling area based on fine amalgam particles is further multiplied if the surfaces are provided with a large number of bumps and recesses by known manufacturing methods, such as pattern rolling, stamping, blasting etc. In addition to enlarging the surface, the grooves in the plates increase the retention effect of relatively fine amalgam powder. The plates can be made of non-metallic material, as well as metallic material. However, metal plates are preferred due to higher affinity for amalgam. The distance between onto each other resting plates in the package should be within the 1–5 mm range and is achieved conveniently from stamped bumps in the plates according to a known pattern from for instance the technology of plate heat exchanger technology. The individual plates in the package are preferably demountably held together with all forms of screws.

According to a particular preferred embodiment of the invention, the spacings between the plates are filled out with packing pieces of 1–5 mm size. Hereby, a liquid element is forced to a labyrinthic and longer distance of flow through the plate package and undergoes a number of bendings and collisions, which has shown to have a favourable effect on the settling of particles of amalgam despite a higher average velocity for the liquid compared to open plate spacing. However, the velocity of the liquid can be kept sufficiently low, which practical examples have shown by reaching a very high degree of separation in a separator according to the invention having plate spacings filled with granules. The packing pieces between the plates promotes further homogenous flow distribution over the plate package cross section and ensures also symmetrical load on all deposition surfaces.

According to yet another preferred embodiment of the invention, the plate spacings are filled with plastic granules having a density slightly lower than water, namely less then 1 g/cm$^3$. Because the granules flows up in water, the reuse of clean granules is facilitated in the reconditioning step of the separator.

Furthermore, to be able to assure slow flow through the separator, a perforated wall is preferably arranged downstream the fine settling zone and in front of the outlet from the separator, the total hole area of said wall being considerably smaller than the hole area of the rest of the perforated walls which preferably delimit the fine distribution zone and the distribution chamber ahead of the same. By the static pressure at the inlet of the separator, normally within the range 0–0.1 kg/CM$^2$ and the flow limiting wall before the outlet, the maximum flow through the separator is totally under control.

BRIEF DESCRIPTION OF THE INVENTION

Figure 2:
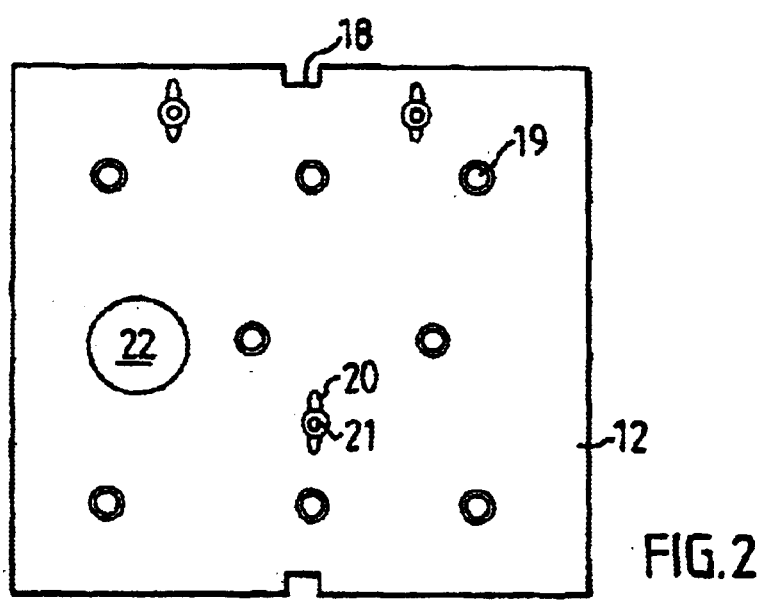

The invention is further illustrated by a preferred embodiment thereof, with reference to the appended drawing, in which FIG. 1 illustrates a vertical section through a schematic separator and FIG. 2 illustrates a plate package from above.

DETAILED DESCRIPTION OF THE INVENTION

The separator according to FIG. 1 consists of a container 1, comprising an inlet 2 in the top at one of its ends and an outlet 3 in the top at the opposite end. In operation, the inlet 2 is connected to a waste-water duct from a dentistry and the outlet 3 to a drainage. From the inlet 2, the water to be cleaned first flows down to a pre-settling chamber 4, where all forms of coarser particles settle. The pre-settling chamber 4 is delimited in the direction of flow by a perforated plate 5, which together with another perforated plate 6 delimit a distribution chamber 7. In the distribution chamber 7, a wire grid 8 is provided to further eliminate possible particles, which could hazard free passage of liquid through all the holes in the plate 6.

Between the distribution plate 6 and another perforated plate 9 is a plate package 10, comprising a plurality of fixed plates 12 spaced apart. The spacings 11 are filled with plastic granules 13. A sealing means 14 between the plate package 10 and a container lid 15, and a sealing means 16 seals the plate package so that all the flow of liquid occurs through the spacings 11 filled with granules.

Behind the plate package 10, but in front of the outlet 3, another plate 17 is provided having holes distributed over the entire cross section of the separator, with a total hole area being substantially smaller than the hole area of each of the perforated plates 5, 6 and 9. The plate 17 thereby provides a flow limiting function for the flow of liquid through the separator.

Fig. 2 shows a plate package 10, demounted from the separator, viewed from above. Notches 18 in each plate 12 correspond with guides in the container 1. A number of bumps 19 form distances between the plates in the package 10. Nuts 20 on top threaded rods 21 through the complete plate package 10 hold it together. In each plate 12, a hole 22 is punched, so that a vertical channel 23 is formed through the plate package 10 for refilling packing pieces 13 when the plate package 10 is positioned into the container 1.

In addition to the described embodiment, it will be understood that variations and modifications can be made within the scope of the invention as described in the appended claims. For instance, the plates can be corrugated or have wave shaped surfaces instead of flat worked surfaces. Instead of a single plate package, several plate packages can be coupled serial to the first one, whereby both, one or none thereof are filled with granules in the plate spacings.

Furthermore, the space distribution between the different zones in the separator, can vary depending on application. If, for instance, the load at a certain dentistry is unusually high, but still long operation time before exchange of separator is required, the pre-settling zone 4 in the illustrated separator can be exchanged by, for instance a whole separate container 1, which is empty or just contains one or more coarse separation nets or similar.

What is claimed is:

1. An apparatus for separation of particles from a liquid, comprising:
    a container having an inlet for particle contaminated liquid,
    a pre-settling zone in communication with said inlet for settling of coarser particles, the pre-settling zone delimited by a perforated plate extending from a top of said container to a bottom of said container,
    a distribution chamber in communication with said pre-settling zone for uniform distribution of liquid flow into a fine settling zone communicating with an outlet for purified liquid, the distribution chamber delimited by another perforated plate extending from the top of said container to the bottom of said container;
    said fine settling zone comprising at least one plate package comprising a plurality of parallel fixed plates, stacked horizontally;
    each fixed plate having at least on a top surface a plurality of bumps and recesses.

2. An apparatus for separation of particles from a liquid, comprising:
    a container having an inlet for particle contaminated liquid;
    pre-settling zone in communication with said inlet for settling of coarser particles;
    a distribution chamber in communication with said pre-settling zone for uniform distribution of liquid flow into a fine settling zone communicating with an outlet for purified liquid,
    said fine settling zone comprising at least one plate package comprising a plurality of parallel fixed plates, stacked horizontally and having spacings between each other ranging between 1 to 5 mm,
    each fixed plate having at least on a top surface a plurality of bumps and recesses;
    a first perforated element separating the pre-settling zone from the distribution chamber;
    a second perforated element separating the distribution chamber from the fine settling zone; and
    a perforated wall between the fine settling zone and the outlet,
    said perforated wall having a total hole area which is substantially smaller than a total hole area of each of said perforated elements.

3. The apparatus according to claim 2, wherein the plate spacings between the plates are filled with packing pieces having a size of 1 to 5 mm.

4. The apparatus according to claim 3, wherein the packing pieces consist of plastic granules having a density of less than 1 g/cm$^3$.

5. The apparatus according to claim 2, wherein the plates in the plate package are made of metal.

6. The apparatus according to claim 2, wherein the plate package comprises 30–60 parallel fixed plates, each plate having a surface of 2 dm$^2$.

7. The apparatus according to claim 2, wherein the distribution chamber comprises a wire grid for further elimination of particles.

8. The apparatus according to claim 2, further comprising a third perforated plate upstream of said perforated wall and downstream of said plate package.

9. An apparatus for separation of particles from a liquid, comprising:
    a container having an inlet for particle contaminated liquid;
    pre-settling zone in communication with said inlet for settling of coarser particles;
    a distribution chamber in communication with said pre-settling zone for uniform distribution of liquid flow into a fine settling zone communicating with an outlet for purified liquid,
    said fine settling zone comprising at least one plate package comprising a plurality of parallel fixed plates, stacked horizontally and having spacings between each other ranging from 1 to 5 mm,
    each fixed plate having at least on a top surface a plurality of bumps and recesses,
    wherein the container has a lid and a bottom, and sealing means are provided between the lid and the plate package, and between the bottom and the plate package, whereby all liquid flow occurs through the plate spacings between the parallel fixed plates.

10. An apparatus for separation of particles from a liquid, comprising:
- a container having an inlet for particle contaminated liquid;
- a pre-settling zone in communication with said inlet for settling of coarser particles;
- a distribution chamber in communication with said pre-settling zone for uniform distribution of liquid flow into a fine settling zone communicating with an outlet for purified liquid,
- said fine settling zone comprising at least one plate package comprising a plurality of parallel fixed plates, stacked horizontally,
- each fixed plate having at least on a top surface a plurality of bumps and recesses;
- a first perforated element separating the pre-settling zone from the distribution chamber;
- a second perforated element separating the distribution chamber from the fine settling zone; and
- a perforated wall between the fine settling zone and the outlet,
- said perforated wall having a total hole area which is substantially smaller than a total hole area of each of said perforated elements.

11. The apparatus according to claim 10, further comprising a third perforated plate upstream of said perforated wall and downstream of said plate package.

12. The apparatus according to claim 10, wherein the plates in the plate package are made of metal.

13. The apparatus according to claim 10, wherein the plate package comprises 30–60 parallel fixed plates, each plate having a surface of 2 dm$^2$.

14. The apparatus according to claim 10, wherein the distribution chamber comprises a wire grid for further elimination of particles.

15. The apparatus according to claim 10, wherein the container has a lid and a bottom, and sealing means are provided between the lid and the plate package, and between the bottom and the plate package, whereby all liquid flow occurs through the plate spacings between the parallel fixed plates.

16. The apparatus according to claim 10, wherein each fixed plate in the plate package has at least one hole for filling packing pieces when the plate package is placed in the container, and the plate spacings between the plates are filled with packing pieces having a size of no more than 5 mm.

17. The apparatus according to claim 16, wherein the packing pieces consist of plastic granules having a density of less than 1 g/cm$^3$.

* * * * *